United States Patent
Heidemann et al.

(10) Patent No.: US 9,687,838 B2
(45) Date of Patent: Jun. 27, 2017

(54) PROCESS FOR THE REGENERATION OF A SUPPORTED NOBLE METAL CATALYST

(71) Applicants: BASF SE, Ludwigshafen (DE); DOW GLOBAL TECHNOLOGIES LLC, Midland, MI (US)

(72) Inventors: Thomas Heidemann, Viernheim (DE); Barbara Becker, Moerlenbach (DE)

(73) Assignees: BASF SE, Ludwigshafen (DE); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/899,444

(22) PCT Filed: Jun. 17, 2014

(86) PCT No.: PCT/EP2014/062671
§ 371 (c)(1),
(2) Date: Dec. 17, 2015

(87) PCT Pub. No.: WO2014/202577
PCT Pub. Date: Dec. 24, 2014

(65) Prior Publication Data
US 2016/0144353 A1    May 26, 2016

(30) Foreign Application Priority Data
Jun. 17, 2013 (EP) .................................... 13172299

(51) Int. Cl.
| | | |
|---|---|---|
| *C07C 29/00* | (2006.01) | |
| *B01J 23/00* | (2006.01) | |
| *B01J 38/48* | (2006.01) | |
| *B01J 38/02* | (2006.01) | |
| *B01J 38/60* | (2006.01) | |
| *B01J 38/62* | (2006.01) | |
| *B01J 38/64* | (2006.01) | |
| *B01J 38/66* | (2006.01) | |
| *B01J 23/96* | (2006.01) | |
| *C07C 29/157* | (2006.01) | |
| *B01J 23/44* | (2006.01) | |
| *C07C 29/132* | (2006.01) | |

(52) U.S. Cl.
CPC ............... *B01J 38/48* (2013.01); *B01J 23/44* (2013.01); *B01J 23/96* (2013.01); *B01J 38/02* (2013.01); *B01J 38/60* (2013.01); *B01J 38/62* (2013.01); *B01J 38/64* (2013.01); *B01J 38/66* (2013.01); *C07C 29/132* (2013.01); *C07C 29/157* (2013.01); *Y02P 20/584* (2015.11)

(58) Field of Classification Search
CPC .......... C07C 29/132; B01J 38/00; B01J 23/00
USPC ........ 568/864; 502/22, 25, 27, 333; 549/531
See application file for complete search history.

(56) References Cited

U.S. PATENT DOCUMENTS

| | | | |
|---|---|---|---|
| 5,695,634 A | 12/1997 | Neuenfeldt et al. | |
| 6,518,449 B1 | 2/2003 | Boschat et al. | |
| 7,026,493 B2 * | 4/2006 | Teles ................... | C07D 301/12 549/531 |
| 2011/0008238 A1 | 1/2011 | Radius et al. | |

FOREIGN PATENT DOCUMENTS

| | | |
|---|---|---|
| EP | 0 200 260 | 12/1986 |
| WO | 02 062779 | 8/2002 |
| WO | 2007 074101 | 7/2007 |

OTHER PUBLICATIONS

International Search Report issued Aug. 12, 2014 in PCT/EP2014/062671 filed Jun. 17, 2014.
Written Opinion of the International Searching Authority issued Aug. 12, 2014 in PCT/EP2014/062671 filed Jun. 17, 2014.
Ullmann's Encycolpedia of Industrial Chemistry, 5th edition, Antidiabetic Drugs to Benzoquinone and naphthoquinone Dyes, vol. 3, 1989, pp. 447-457.
International Preliminary Report on Patentability and Written Opinion issued Dec. 30, 2015 in PCT/EP2014/062671 filed Jun. 17, 2014.

* cited by examiner

*Primary Examiner* — Sikarl Witherspoon
(74) *Attorney, Agent, or Firm* — Oblon, McClelland, Maier & Neustadt, L.L.P.

(57) ABSTRACT

A process for the regeneration of a supported noble metal catalyst comprising contacting the catalyst with a liquid aqueous system at a temperature in the range of from 90 to 160° C., wherein the pH of the aqueous system is outside the range of from 6 to 8, separating the aqueous system from catalyst; and subjecting the catalyst to calcination.

17 Claims, No Drawings

PROCESS FOR THE REGENERATION OF A SUPPORTED NOBLE METAL CATALYST

The present invention relates to a process for the regeneration of a supported noble metal catalyst having been used in a process comprising reducing a hydroperoxypropanol.

The epoxidation of olefins, in particular the epoxidation of propene, is an important industrial-scale process since the epoxidation products, in particular propylene oxide, is a starting material for the production of various polymers. One of the most prominent epoxidation processes is the epoxidation making use of hydrogen peroxide as epoxidizing agent. Preferably in these processes, titanium containing zeolites are employed as catalytically active components, for example titanium silicalite-1 (TS-1) or Ti-MWW. Usually, solvents are used for the epoxidation process, among which methanol and acetonitrile are most preferred. In particular, methanol is used as solvent if a TS-1 based catalyst is employed as epoxidation catalyst.

Among the by-products or side-products possibly obtained in the course of the epoxidation, oxygenates are to be mentioned, including, for example, alkoxyalcohols, glycols and alpha-hydroperoxyalcohols. If, for example, the solvent used during the epoxidation reaction is methanol and the compound to be epoxidized is propene, by-products or side-products of the above-mentioned types may include 2-methoxy-1-propanol, 1-methoxy-2-propanol, propylene glycol, 2-hydroperoxy-1-propanol and 1-hydroperoxy-2-propanol.

Hydroperoxypropanols are usually thermally labile and may tend to decompose quickly. Compounds resulting from such decomposition generally include formaldehyde, acetaldehyde, propylene glycol and hydroxyacetone. Some of these compounds in turn tend to be converted further, and the respective compounds include, for example, formaldehyde dimethyl acetal, formic acid and methyl formate, acetaldehyde dimethyl acetal, acetic acid and methyl acetate. Some of these compounds such as acetaldehyde and methyl formate can be separated by distillation from a reaction mixture comprising the epoxide only with great difficulty. Further, in particular in industrial-size processes, process streams such as solvent streams are recycled due to economical reasons, and accumulation of said by-products and side-products has to be avoided.

Thus, an effective separation of hydroperoxypropanols must be performed in the course of the workup of the epoxidation reaction mixture. Typically, in the course of the workup, a mixture containing hydroperoxypropanol is subjected to reduction. In this reduction, the hydroperoxypropanols are reduced to the corresponding glycols, and further decomposition and the formation of the above-described undesirable components is avoided.

The reduction of hydroperoxypropanol may be carried out using all reducing agents described for this purpose in literature, described, for example, in WO 02/062779 A. However, preference is given to hydrogen in the presence of a suitable heterogeneous hydrogenation catalyst. The hydrogenation catalyst comprises typically at least one active metal of group VIIb, VIII, Ia or Ib of the Periodic Table of Elements impregnated on a suitable support material. Reference is made, for example, to WO 2007/074101 A where Pd, Pt, Rh, Ir, Os, and combinations of two or more thereof are described as catalytically active metals.

Usually, such heterogenous catalysts tend to deactivate if they are on stream for a certain period of time. In order to avoid a mere replacement of such a deactivated catalyst with a fresh catalyst, it is generally desirable to subject the deactivated catalyst to a regeneration stage. Certainly, the specific regeneration conditions to be applied strongly depend on the reaction the deactivated catalyst had been used for since this reaction, namely the compounds the catalyst gets in contact with and the respective reaction conditions, will significantly attribute to the specific deactivation.

Regarding such regeneration, WO 2007/074101 A discloses two possibilities. The first possible regeneration consists of a treatment of the deactivated catalyst with at least one suitable solvent. As preferred solvents, those used in the epoxidation process as starting materials, solvents, products or by-products are mentioned. Explicitly, hydrogen peroxide solutions, for example aqueous hydrogen peroxide solutions, optionally containing, for example, methanol, or methanol, for example as aqueous methanolic solution, propylene oxide, for example as aqueous propylene oxide solution, optionally additionally containing methanol, propylene glycol, for example 1,2-dihydroxypropane, optionally additionally containing methanol and/or water, methoxypropanol, or mixtures of two or more of these compounds and/or solutions are mentioned. As second possible regeneration, a thermal treatment, in particular a treatment at elevated temperature compared to room temperature in the presence of a gas comprising oxygen is disclosed. Preferred thermal treatments disclosed in WO 2007/074101 A include a drying stage at temperatures of up to 200° C. and a calcination stage at temperatures of up to 400° C., each under an atmosphere comprising from 1 to 10 volume-%, more preferably from 2 to 8 volume-% of oxygen. Further, it is disclosed that these two possible regeneration processes can be combined. In the examples of WO 2007/074101 A, no regeneration of the catalyst is described.

Generally, using mixtures as described in WO 2007/074101 A for the regeneration of the catalyst, which mixtures are described as preferably being mixtures obtained from specific process stages according to the process as described in WO 2007/074101 A—referred to therein as stages (c) and (d) and/or (e), the mixtures being referred to as mixtures (Mb1), (Mb2), (Mc2i) and/or (Mc2ii)—may provide a certain advantage, due to the mere availability of these mixtures. Nevertheless, these mixtures may contain, for example, organic material which in turn could lead to a certain deactivation of the catalyst. Further, using such mixtures which contain organic material in a considerable amount would necessitate a scrupulous washing of the thus treated catalyst in order to guarantee an essentially organic material-free regenerated catalyst.

Therefore, it was an object of the present invention to provide an advantageous process for the regeneration of a supported noble metal catalyst having been used in a process comprising reducing a hydroperoxypropanol. In particular, it was an object of the present invention to provide an advantageous process for the regeneration of a supported noble metal catalyst having been used in a process comprising reducing a hydroperoxypropanol contained in a mixture obtained in the course of working up an epoxidation reaction mixture. It was a further object of the present invention to provide an effectively regenerated supported noble metal catalyst whose activity is comparable with the activity of a respective fresh catalyst when used for reducing a hydroperoxypropanol, in particular a hydroperoxypropanol contained in a mixture obtained in the course of working up an epoxidation reaction mixture.

According to the present invention, it was found that such a regeneration process can be provided if a supported noble metal catalyst having been used in a process comprising reducing a hydroperoxypropanol is treated with a non-pH-neutral liquid aqueous system at elevated temperatures and is subjected to calcination after the treatment with said liquid aqueous system.

From this regeneration process of the present invention, surprisingly, a regenerated catalyst could be obtained whose conversion rate and operating time are nearly as good or the same as the conversion rate and operating time of a respective fresh catalyst when used in the reduction of hydroperoxypropanol under otherwise identical reaction conditions.

These unexpected findings indicate that by using the regeneration process of the present invention essentially all contaminations are removed from the supported noble metal catalyst in a simple and effective manner.

Thus, the present invention relates to a process for the regeneration of a supported noble metal catalyst having been used in a process comprising
(a) providing a mixture containing water, an organic solvent and a hydroperoxypropanol;
(b) treating the mixture provided in (a) in a reactor under reducing conditions with hydrogen in the presence of the supported noble metal catalyst to obtain a mixture containing water, the organic solvent and propylene glycol;
said process for the regeneration comprising
(c) separating the mixture obtained from (b) from the catalyst;
(d) contacting the separated catalyst with a liquid aqueous system at a temperature in the range of from 90 to 160° C., wherein the pH of the aqueous system is outside the range of from 6 to 8;
(e) separating the aqueous system from the catalyst;
(f) subjecting the catalyst to calcination.

Step (a)

According to step (a) of the present invention a mixture containing water, an organic solvent and a hydroperoxypropanol is provided.

Generally, there are no specific restrictions how this mixture is provided. Preferably, the mixture is obtained from one or more of work-up stages downstream an epoxidation reaction, more preferably from one or more of work-up stages downstream an epoxidation reaction wherein propene is epoxidized with hydrogen peroxide in the presence of a catalyst, preferably a catalyst which contains, as catalytically active agent, a titanium containing zeolite. The epoxidation reaction of stage (a) of the inventive process is preferably carried out in a solvent, with methanol or acetonitrile as solvent being preferred, and methanol being especially preferred. Optionally, a solvent mixture comprising methanol and at least one other suitable solvent can be employed. Preferably, a solvent mixture of methanol and water is used. If the epoxidation reaction is carried out in a solvent mixture comprising water, the water may be introduced as such and/or via, e.g., an aqueous hydrogen peroxide solution.

The epoxidation reaction can be conducted in one, two, three or more stages. Preferably, the reaction is conducted in one, two or three stages, more preferably in one or two stages and especially preferably in two stages. Preferably, the epoxidation reaction comprises at least one, such as one, two, three or more, preferably one or two, still more preferably one intermediate separation stage between two subsequent epoxidation reaction stages. Further preferably, propene which has not been reacted in the epoxidation reaction upstream the intermediate separation stage is separated in the at least one intermediate separation stage. Therefore, the epoxidation process preferably comprises at least the following sequence of stages (i) to (iii):

(i) reacting propene with hydrogen peroxide in the presence of a titanium zeolite catalyst to give a mixture comprising propylene oxide, unreacted propene, unreacted hydrogen peroxide, methanol and water;
(ii) separating the propylene oxide and the unreacted propene from the mixture resulting from stage (i) to give a mixture comprising unreacted hydrogen peroxide, methanol and water,
(iii) reacting fresh propene with the unreacted hydrogen peroxide in the mixture resulting from stage (ii).

As to stages (i) and (iii), there are no specific restrictions as to how the reaction is carried out. Accordingly, it is possible to carry out one of the reaction stages in batch mode or in semi-continuous mode or in continuous mode and independently thereof, the other reaction stage in batch mode or in semi-continuous mode or in continuous mode. Preferably, both reaction stages (i) and (iii) are carried out in continuous mode.

As mentioned above, the epoxidation reaction, in particular the epoxidation reaction in stages (i) and (iii), is preferably carried out in the presence of at least one titanium zeolite catalyst. Specific mention may be made of titanium containing zeolites having a pentasil zeolite structure, in particular the types which can be assigned X-ray-crystallographically to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YNU, YUG and ZON, and also mixed structures of two or more of the abovementioned structures. Furthermore, titanium-containing zeolites having the ITQ-4, SSZ-24, TTM-1, UTD-1, CIT-1 or CIT-5 structure are also conceivable for use in the process of the invention. Further titanium-containing zeolites which may be mentioned are those having the ZSM-48 or ZSM-12 structure. For the purposes of the present invention, preference is given to using Ti zeolites having an MFI structure, an MEL structure, an MFI/MEL mixed structure or an MWW structure. Further preference is given specifically to the Ti-containing zeolite catalysts which are generally referred to as "TS-1", "TS-2", TS-3", and also Ti zeolites having a framework structure isomorphous with beta-zeolite. Very particular preference is given to using zeolite catalysts TS-1 and Ti-MWW, particularly to using a TS-1 zeolite catalyst.

The titanium zeolite catalyst can be employed as powder, as granules, as microspheres, as shaped bodies having, for example, the shape of pellets, cylinders, wheels, stars, spheres and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm. In order to increase the bulk density of the extrudates, it is preferred to cut the extrudates with a stream essentially consisting of an inert gas. Most preferably, a TS-1 or Ti-MWW catalyst is employed which is produced by first forming microspheres, for example microspheres formed by spray-drying or spray-granulation such as described, for example, in EP 0 200 260 A, and then forming said microspheres to obtain shaped bodies, preferably extrudates as described above. For each of these forming or shaping methods according to which catalyst powder is processed to give shaped bodies such as microspheres, extrudates, granules, pellets, and the like, it is possible to use at least one additional binder and/or at least one pasting agent and/or at least one pore forming agent. Prior to using the catalyst in the epoxidation reaction of the present invention, it is possible to suitably pre-treat the catalyst. In case the catalyst is used as supported catalyst, carriers can be preferably used which are inert, i.e. which do not react with hydrogen peroxide, propene, and propylene oxide. As to the geometry of the shaped bodies, there are no specific restrictions as long as the catalyst is kept in fixed-bed state. Shaped bodies such as pellets, spheres, cylinders and the like can be employed. Preferred diameters are from 1 to 35 mm, more preferably from 1.5 to 30 mm and more preferably from 2 to 10 mm.

The reactions in stages (i) and (iii) are preferably carried out in suspension mode or fixed-bed mode, most preferably in fixed-bed mode. Generally, it is possible to use the same or different types of reactors in stages (i) and (iii). Thus, it is possible to carry out one of the reaction stages in an isothermal or adiabatic reactor and the other reaction stage, independently thereof, in an isothermal or adiabatic reactor. The term "reactor" as used in this respect comprises a single reactor, a cascade of at least two serially connected reactors, at least two reactors which are operated in parallel, or a multitude of reactors, wherein at least two reactors are serially coupled and wherein at least two reactors are operated in parallel. According to a preferred embodiment, stage (i) of the present invention is carried out in at least two reactors which are operated in parallel, and stage (iii) of the present invention is carried out in a single reactor. Each of the reactors described above, especially the reactors according to the preferred embodiment, can be operated in downflow or in upflow operation mode.

In case the reactors are operated in downflow mode, it is preferred to use fixed-bed reactors which are preferably tubular, multi-tubular or multi-plate reactors, most preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least 40° C. and the maximum temperature in the catalyst bed is 60° C. In case of downflow operation of the reactors, it is possible to choose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

In case the reactors are operated in upflow mode, it is preferred to use fixed-bed reactors. It is still further preferred to use at least two fixed-bed reactors in stage (i) and at least one reactor in stage (iii). According to a still further embodiment, the at least two reactors used in stage (i) are serially connected or operated in parallel, more preferably operated in parallel. Generally, it is necessary to equip at least one of the reactors used in stage (i) and/or (iii) with a cooling means such as a cooling jacket in order to remove at least partially the heat resulting from reaction in the respective reactor. Especially preferably, at least two reactors are employed in stage (i) which are connected in parallel and can be operated alternately. In case the reactors are operated in upflow mode, the two or more reactors connected in parallel in stage (i) are particularly preferably tube reactors, multi-tube reactors or multi-plate reactors, more preferably multi-tube reactors and especially preferably shell-and-tube reactors comprising a multitude of tubes such as from 1 to 20,000, preferably from 10 to 10,000, more preferably from 100 to 9,000, more preferably from 1,000 to 8,000 and particularly preferably from 3,000 to 7,000, tubes. In stage (iii), particular preference is given to using a shaft reactor, more preferably a continuously operated shaft reactor and particularly preferably a continuously operated, adiabatic shaft reactor.

According to the present invention, it is also possible to use two or more of these reactors such as two, three or four of these reactors which are serially coupled or coupled in parallel, more preferably in parallel. Therefore, the present invention also relates to a process as described above wherein in stage (i), at least two shell-and-tube reactors each having of from 1 to 20.000 internal tubes and being continuously operated in upflow mode, said reactors being operated in parallel, are employed, and wherein in stage (iii), one adiabatic shaft reactor or two adiabatic shaft reactors being continuously operated in upflow mode, are employed. Still more preferably, the reaction in at least one of these reactors, more preferably in the at least two reactors of stage (i) and still more preferably in all reactors used in states (i) and (iii) is conducted such that in the respective reactor, a single liquid phase is present. Even more preferably, in each of the reactors used in stages (i) and (iii), the catalyst used for the epoxidation reaction is employed as fixed-bed reactor wherein the catalyst is a titanium zeolite catalyst, more preferably a TS-1 or Ti-MWW catalyst and even more preferably a TS-1 catalyst.

Depending on the specific characteristics of the catalyst which is used as fixed-bed catalyst, it may be necessary to use at least one additional inert compound in order to keep the catalyst, for example the catalyst in the form of shaped bodies such as extrudates or the like, in fixed-bed state. Thus, at least one layer of shaped bodies consisting or essentially consisting of the at least one inert compound can be arranged below or above or below and above a catalyst layer such forming, for example, a sandwich structure. This concept can also be applied to horizontally arranged reactors. In this context, the term "inert compound" relates to a compound which does not participate in the reaction or reactions carried out in the reactor in which the inert compound is employed. As to the present epoxidation reaction, preferred inert compounds are, for example, steatite, high-fired alpha-alumina, carbides, silicides, nitrides, oxides, ceramics, non-acidic glasses, suitable metals such as steels of types 1.4306, 1.4307, 1.4541, 1.4571 or comparable materials. Such inert compounds can be used in at least one of the reactors used in (i) and/or (iii).

The hydrogen peroxide is used in the process according to the invention preferably in the form of an aqueous solution with a hydrogen peroxide content generally of from 1 to 90 weight-%, preferably of from 10 to 70 weight-%, more preferably from 10 to 60 weight-%. A solution having of from 20 to less than 50 weight-% of hydrogen peroxide is particularly preferred. Further, it is conceivable to employ a crude aqueous hydrogen peroxide solution. As crude aqueous hydrogen peroxide solution, a solution can be used which is obtained by extraction of a mixture with essentially pure water wherein the mixture results from a process known as anthraquhinone process (Ullmann's Encycolpedia of Industrial Chemistry, 5th edition, volume 3 (1989) pages 447-457). In this process, the hydrogen peroxide formed is generally separated by extraction from the working solution. This extraction can be performed with essentially pure water, and the crude aqueous hydrogen peroxide is obtained. This crude solution can be employed without further purification. It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back. Of course, the preparation of hydrogen peroxide from the elements is also possible.

The reaction in the reactors according to stage (i) is preferably carried out at reaction conditions such that the hydrogen peroxide conversion is at least 80%, more preferably at least 85% and still more preferably at least 90%. The pressure in the reactors is preferably in the range of from 10 to 30 bar, more preferably from 15 to 25 bar. The temperature of the cooling water passed through the cooling jackets of the at least one reactor is in the range of preferably from 20 to 70° C., more preferably from 25 to 65° C. and particularly preferably from 30 to 60° C.

Preferably, the product mixture obtained from stage (i) essentially consists of propylene oxide, unreacted propene, methanol, water, and unreacted hydrogen peroxide, and optionally propane which can be contained in the propene starting material.

According to stage (ii), propylene oxide and unreacted propene are separated from the mixture resulting from stage (i). This separation can be conducted by essentially every suitable method. Preferably, this separation is carried out by distillation using at least one distillation column. The reaction mixture obtained from the at least one reactor, preferably from the at least two reactors used in stage (i), comprising unreacted propene, propylene oxide, methanol, water and unreacted hydrogen peroxide and optionally propane, is introduced in the distillation column. The distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. Preferably, the distillation column has from 5 to 60, preferably from 10 to 50 and especially preferably from 15 to 40 theoretical stages.

The temperature of the product mixture obtained from stage (i) is preferably in the range of from 40 to 60° C., more preferably of from 45 to 55° C. Prior to being fed to the distillation column of (ii), the product mixture is preferably heated up in at least one heat exchanger to a temperature in the range of from 50 to 80° C., more preferably of from 60 to 70° C.

At the top of the distillation column of (ii), a stream essentially consisting of propylene oxide, methanol, and unreacted propene and optionally propane, is obtained. At the top of the column, a mixture is obtained having a water content of not more than 0.5 weight-%, preferably of not more than 0.4 weight-% and still more preferably of not more than 0.3 weight-%, and having a hydrogen peroxide content of not more than 100 ppm, preferably of not more than 20 ppm and still more preferably of not more than 10 ppm, in each case based on the total weight of the mixture obtained at the top of the column.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

Preferably, the distillation column used in (ii) is configured as dividing wall column having at least one side-offtake, preferably one side-offtake. Preferably, the dividing wall column preferably has from 20 to 60, more preferably from 30 to 50 theoretical stages. The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical stage. In the above mentioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

The differential pressure over the dividing wall column can be utilized as regulating parameter for the heating power. The distillation is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar. The distillation is then preferably carried out in a temperature range from 65 to 100° C., more preferably from 70 to 85° C. The distillation temperature is measured at the bottom of the tower. In case such a divided wall column is used, at the top of the distillation column of (ii), a stream essentially consisting of propylene oxide, methanol, and unreacted propene, is obtained.

At the top of the column, a mixture is obtained having a water content of not more than 500 ppm, preferably of not more than 400 ppm, and still more preferably of not more than 300 ppm, and having a hydrogen peroxide content of not more than 50 ppm, preferably of not more than 20 ppm and still more preferably of not more than 10 ppm, in each case based on the total weight of the mixture obtained at the top of the column. Furthermore, the top stream obtained has a propene content of from 15 to 35 weight-%, preferably of from 20 to 30 weight-% and still more preferably of from 20 to 25 weight-%, a propylene oxide content of from 50 to 80 weight-%, preferably of from 55 to 75 weight-% and especially preferably of from 60 to 70 weight-%, and a methanol content of from 5 to 20 weight-%, more preferably of from 7.5 to 17.5 weight-% and especially preferably of from 10 to 15 weight-%, in each case based on the total weight of the top stream.

At the side-offtake of the distillation column, a stream essentially consisting of methanol and water is obtained. At the side-offtake of the column, a mixture is obtained having a methanol content of at least 95 weight-%, preferably at least 96 weight-% and still more preferably at least 97 weight-%, and having a water content of not more than 5 weight-%, preferably of not more than 3.5 weight-% and still more preferably of not more than 2 weight-%, in each case based on the total weight of the mixture obtained at the side-offtake of the column. At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column. At least part of the stream taken from the side of the dividing wall column can be recycled as solvent into stage (i) of the inventive process. Preferably, at least 90%, more preferably at least 95% of the stream taken from the side-offtake are recycled into stage (i).

The bottoms stream taken from the distillation column, preferably the dividing wall distillation column, essentially consisting of methanol, water and unreacted hydrogen peroxide, is then fed to the reactor of stage (iii). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Fresh propene is added directly into the reactor of stage (iii) or added to the bottoms stream obtained from (ii) prior to introducing same into the reactor of stage (iii). Alternatively or additionally, fresh hydrogen peroxide can be added.

The reaction mixture obtained from stage (iii) preferably has a methanol content of from 50 to 90 weight-%, more preferably of from 60 to 85 weight-% and especially preferably of from 70 to 80 weight-%, based on the total weight of the reaction mixture. The water content is preferably in the range of from 5 to 45 weight-%, more preferably of from 10 to 35 weight-% and especially preferably of from 15 to 25 weight-%, based on the total weight of the reaction mixture. The propylene oxide content is preferably in the range of from 1 to 5 weight-%, more preferably of from 1 to 4 weight-% and especially preferably of from 1 to 3 weight-%, based on the total weight of the reaction mixture. The propene content is preferably in the range of from 0 to 5 weight-%, more preferably of from 0 to 3 weight-% and especially preferably of from 0 to 1 weight-%, based on the total weight of the reaction mixture.

The product mixture taken from the reactor of stage (iii) can be subjected directly, without any intermediate stage, to the propylene oxide separation of stage (a).

If unreacted propene is present in the mixture taken from the reactor of stage (iii), it may desirable to at least partially separate propene from this mixture prior to separation of propylene oxide. In this case, at least a portion of the stream taken from the top of the distillation column of stage (ii) can be combined with the product mixture taken from the reactor of stage (iii) to give a mixture which is then fed to propene separation. Alternatively, it is possible to separately feed the product mixture obtained from stage (iii) and at least a portion of the top stream of the distillation column of stage (ii) into propene separation.

Either from the mixture obtained from stage (iii) or from the mixture obtained from propene separation, as described above, propylene oxide is preferably separated in stage (a) of the inventive process. This separation can be conducted by every suitable method. Most preferably, separation is conducted by distillation which is preferably carried out in at least one distillation column, more preferably in one distillation column. Preferably, this column has of from 30 to 110, more preferably of from 40 to 100 and especially preferably of from 50 to 90 theoretical stages. The distillation column is preferably operated at a top pressure of from 1 bar or less. Especially preferably, the distillation column is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

Therefore, the present invention relates to the process as described above, wherein the mixture provided in (a) is obtained by a process for the epoxidation of propene, said process comprising reacting propene with hydrogen peroxide in the presence of the organic solvent and a titanium zeolite catalyst, and separating propylene oxide and optionally propene from the resulting epoxidation reaction mixture to obtain the mixture provided in (a).

According to this preferred distillative propylene oxide separation of stage (a), a mixture is obtained as bottom stream comprising water and at least 55 weight-% of methanol. According to a preferred embodiment of the inventive process, the mixture comprises of from 55 to 85 weight-%, more preferably from 65 to 80 weight-% and especially preferably from 75 to 79 weight-% of methanol, and of from 10 to 40 weight-%, more preferably from 15 to 30 weight-% and especially preferably of from 20 to 25 weight-% of water. The propylene oxide content of this mixture is preferably at most 500 ppm, more preferably at most 300 ppm and still more preferably at most 100 ppm. The propene content of this mixture is preferably at most 100 ppm, more preferably at most 50 ppm and still more preferably at most 10 ppm.

According to an alternative of stage (a), the reaction mixture obtained from stage (iii), alone or optionally in combination with the top stream obtained from separation stage (ii), can be subjected to a first separation stage where propene and propylene oxide are suitably separated together, preferably by distillation in at least one distillation column, to obtain a mixture (Ma) comprising water and at least 55 weight-% of methanol, and another mixture comprising propene and propylene oxide. Distillation is preferably carried out in at least one distillation column, more preferably in one distillation column. Preferably, this column has of from 30 to 110, more preferably of from 40 to 100 and especially preferably of from 50 to 90 theoretical stages. Distillation is preferably performed at a pressure of from 1 to 20 bar, more preferably from 2 to 10 bar and still more preferably from 3 to 7 bar. From the latter mixture, propylene oxide can be separated. Propene thus obtained can be recirculated as starting material into the epoxidation reaction, preferably into stage (i) and/or stage (iii). The mixture thus obtained preferably comprises of from 55 to 85 weight-%, more preferably from 65 to 80 weight-% and especially preferably from 75 to 79 weight-% of methanol, and of from 10 to 40 weight-%, more preferably from 15 to 30 weight-% and especially preferably of from 20 to 25 weight-% of water. The propylene oxide content of this mixture is preferably at most 500 ppm, more preferably at most 300 ppm and still more preferably at most 100 ppm. The propene content of this mixture is preferably at most 100 ppm, more preferably at most 50 ppm and still more preferably at most 10 ppm.

Generally, the mixture provided in (a) may contain the water, the organic solvent, preferably methanol or acetonitrile, more preferably methanol, and the hydroperoxypropanol in any conceivable amounts. In particular, in case the mixture is provided as downstream mixture in an epoxidation process, the amounts of the water, the organic solvent, preferably methanol or acetonitrile, more preferably methanol, and the hydroperoxypropanol will depend on the specific downstream process stage from which the mixture is obtained. Preferably, in particular if obtained according to the preferred propene epoxidation process as described above, the mixture provided in (a) contains hydroperoxypropanol in an amount in the range of from 0.05 to 5 weight-%, more preferably 0.1 to 3 weight-%, more preferably 0.1 to 2 weight-% based on the weight of the mixture. It is particularly preferred that the mixture provided in (a) contains hydroperoxypropanol in an amount in the range of from 0.1 to 1 weight-% based on the weight of the mixture.

As mentioned above, in addition to the oxygenate hydroperoxypropanol, further oxygenates may be formed in the initial epoxidation reaction or in subsequent working-up stages. Preferably, the mixture provided in (a) additionally contains an oxygenate in an amount in the range of from 0.1 to 1 weight-%, preferably from 0.1 to 0.5 weight-% based on the weight of the mixture, wherein the oxygenate is preferably selected from the group consisting of formaldehyde, acetaldehyde, propionaldehyde, hydroxyacetone, methylformate, dimethoxymethane, and combinations of two or more thereof. Further, the mixture provided in (a) may contain traces of hydrogen peroxide starting material.

Therefore, the mixture provided in (a) preferably comprises of from 55 to 90 weight-%, more preferably from 65 to 87 weight-%, more preferably from 75 to 85 weight-% of the organic solvent, preferably of methanol or acetonitrile, more preferably of methanol, of from 10 to 40 weight-%, more preferably from 15 to 30 weight-% more preferably of from 20 to 25 weight-% of the water, and from 0.05 to 5 weight-%, more preferably from 0.1 to 3 weight-%, more preferably from 0.1 to 2 weight-%, more preferably from 0.1 to 1 weight-% of the hydroperoxypropanol, in each case based on the total weight of the mixture. The propylene oxide content of this mixture is preferably at most 500 ppm, more preferably at most 300 ppm and still more preferably at most 100 ppm. The propene content of this mixture is preferably at most 100 ppm, more preferably at most 50 ppm and still more preferably at most 10 ppm.

Preferably, the mixture provided in (a) comprises of from 55 to 90 weight-%, more preferably from 65 to 87 weight-%, more preferably from 75 to 85 weight-% of the organic solvent, preferably of methanol or acetonitrile, more preferably of methanol, of from 10 to 40 weight-%, more preferably from 15 to 30 weight-% more preferably of from 20 to 25 weight-% of the water, from 0.05 to 5 weight-%, more preferably from 0.1 to 3 weight-%, more preferably from 0.1 to 2 weight-%, more preferably from 0.1 to 1 weight-% of the hydroperoxypropanol, and a further oxygenate in an amount in the range of from 0.1 to 1 weight-%, preferably from 0.1 to 0.5 weight-% based on the weight of the mixture, wherein the further oxygenate is preferably selected from the group consisting of formaldehyde, acetaldehyde, propionaldehyde, hydroxyacetone, methylformate, dimethoxymethane, and combinations of two or more thereof, in each case based on the total weight of the mixture. The propylene oxide content of this mixture is preferably at most 500 ppm, more preferably at most 300 ppm and still more preferably at most 100 ppm. The propene content of this mixture is preferably at most 100 ppm, more preferably at most 50 ppm and still more preferably at most 10 ppm.

The hydroperoxypropanol contained in the mixture provided in (a) is preferably selected from the group consisting of 2-hydroperoxypropanol-1, 1-hydroperoxypropanol-2 and combinations of 2-hydroperoxypropanol-1 and 1-hydroperoxypropanol-2. Preferably, the hydroperoxypropanol is a combination of 2-hydroperoxy-propanol-1 and 1-hydroperoxypropanol-2.

Step (b)

In step (b), the mixture provided in (a) is treated in a reactor under reducing conditions with hydrogen in the presence of the supported noble metal catalyst to obtain a mixture containing water, the organic solvent and a propylene glycol.

Generally, it is conceivable to use the noble metal in powder form which noble metal powder can be prepared by various methods known in the art. Most preferably, the catalyst comprises a composite of a noble metal and a support material. The supported catalyst comprises a noble metal which is preferably selected from the group consisting of palladium, platinum, rhodium, ruthenium, iridium, osmium and a combination of two or more thereof. In case palladium is used as noble metal, the catalyst can additionally contain silver. More preferably, the noble metal is selected from the group consisting of palladium, platinum, rhodium, iridium, osmium and a combination of two or more thereof. More preferably, the noble metal is selected from the group consisting of palladium, platinum, rhodium, and a combination of two or more thereof. More preferably, the noble metal is selected from the group consisting of palladium, platinum, and a combination thereof. More preferably, the noble metal is palladium.

All support materials known for this purpose to a person skilled in the art and have sufficient chemical and thermal stability may be used. Examples are porous oxides such as aluminum oxides, silicon dioxides, aluminosilicates, zeolites, titanium oxides, zirconium oxides, zinc oxides, magnesium oxides, rare earth metal oxides, or activated carbon, or combinations or mixtures of two or more thereof. Preferably, aluminum oxides or activated carbon are used. More preferably, alpha-aluminum oxide or activated carbon are used.

The supported catalyst comprises the noble metal preferably in an amount in the range of from 0.01 to 5.0 weight-%, more preferably from 0.05 to 2.0 weight-%, more preferably from 0.1 to 1.0 weight-%, more preferably from 0.2 to 0.5 weight-%, based on the weight of the catalyst.

Therefore, the supported noble metal catalyst preferably comprises, preferably essentially consists of, a noble metal selected from the group consisting of palladium, platinum, and a combination thereof, and a support material the noble metal is supported on, the support material being selected from the group consisting of aluminum oxides and activated carbon, wherein the catalyst comprises the noble metal preferably in an amount in the range of from 0.01 to 5.0 weight-%, more preferably from 0.05 to 2.0 weight-%, more preferably from 0.1 to 1.0 weight-%, more preferably from 0.2 to 0.5 weight-%, based on the weight of the catalyst.

More, preferably, the supported noble metal catalyst preferably comprises, preferably essentially consists of, palladium and a support material the palladium is supported on, the support material being selected from the group consisting of alpha-aluminum oxide and activated carbon, wherein the catalyst comprises the noble metal preferably in an amount in the range of from 0.1 to 1.0 weight-%, more preferably from 0.2 to 0.5 weight-%, based on the weight of the catalyst. Thus, the supported noble metal catalyst is preferably selected from the group consisting of palladium supported on alumina, preferably alpha-alumina, also referred to as Pd/alpha-$Al_2O_3$, and palladium supported on activated carbon, also referred to as Pd/C.

The composites of a noble metal or a combination of two or more thereof and at least one support, known as supported catalysts, can be produced by any method known to the skilled person. For example, such supported catalysts are generally obtainable by impregnating the support with a solution of the noble metal or combinations of two or more thereof. It is also possible to spray the respective solution of the noble metal onto the support or to apply the noble metal by vapor deposition, electrochemical deposition or by precipitation. Thus obtained composites may be brought into a shape suitable for the respective application, for example extrudates or pressed pellets. This can generally be preceded or followed by further steps such as drying, heat treatment and calcination. As precursors of the noble metals, it is in principle possible to use all water-soluble noble metal compounds, for example readily water-soluble salts or complexes of the noble metals, e.g. nitrates, nitrosyl nitrates, chlorides, acetates, formates and sulfates and also chlorometalates. Drying of the catalyst precursors can be carried out by all drying methods known to those skilled in the art. For the purposes of the present invention, the drying process is preferably carried out at from 80 to 150° C., particularly preferably from 80 to 120° C. The calcination of the catalyst precursors can be carried out in any way known to those skilled in the art. For the purposes of the present invention, the catalyst precursors obtained are preferably exposed to a gas stream comprising air or nitrogen at from 150 to 500° C., particularly preferably from 200 to 450° C.

In general, the calcination process can be followed by the activation of the catalyst precursors obtained. Activation can be carried out by all methods known for this purpose to those skilled in the art in which the catalyst precursors are exposed to a reducing atmosphere, for example a hydrogen-containing atmosphere at room temperature or elevated temperature. Preferably, the catalyst precursors comprising a noble metal can be treated with hydrogen at a temperature in the range of from 80 to 250° C., preferably from 80 to 180° C. The duration of the treatment with hydrogen at room temperature or elevated temperatures depends on the concentration of the noble metal or combination or mixture of two or more thereof. The duration of the treatment is preferably in the range of from 0.5 to 24 hours, more preferably from 1 to 5 hours. During activation, the hydrogen is brought into contact with the catalyst generally at from 10 to 1500 l(hydrogen) kg(catalyst)$^{-1}$ h$^{-1}$, preferably from 50 to 1200 l(hydrogen) kg(catalyst)$^{-1}$ h$^{-1}$.

Generally, the treating of the mixture provided in (a) under reducing conditions with hydrogen in (b) can be carried out in any appropriate way. The reaction may be for example carried out in a batch reactor or in at least one semi-continuously operated reactor or in at least one continuously operated reactor. The continuous mode of operation is preferred. The hydrogenation may be further carried out in a suspension method or a fixed-bed method. It is especially preferred to use a fixed-bed reactor comprising the supported noble metal catalyst over which the mixture provided in (a) is passed.

Preferably, the treating in (b) is carried out at a pressure in the range of from 1 to 100 bar(abs), more preferably from 1 to 20 bar(abs), and at a temperature in the range of from 0 to 180° C., more preferably from 25 to 120° C., more preferably from 50 to 85° C. The hydrogen partial pressure during the treating in (b) is preferably in the range of from 1 to 30 bar, preferably from more 1.5 to 25 bar, more preferably from 2 to 20 bar, more preferably from 3 to 15 bar. If the treating in (b) is carried out using a fixed catalyst bed, the residence time of the liquid which is passed over the catalyst is preferably in the range of from 1 s to 1 h, preferably from 10 s to 20 min, more preferably from 30 s to 5 min.

Preferably, the treating in (b) is carried out under an inert gas atmosphere, wherein the inert gas atmosphere may comprise one or more inert gases. Preferably, the inert gas is a noble gas or nitrogen, with nitrogen being especially preferred.

When treating the mixture provided in (a) in a reactor under reducing condition with hydrogen in the presence of the supported noble metal catalyst, the liquid mixture containing at least water, the organic solvent and propylene glycol is obtained.

Preferably, by treating the preferred mixture provided in (a) under reducing conditions with hydrogen, 1-hydroperoxy-2-propanol, 2-hydroperoxy-1-propanol and further hydroxyacetone are essentially completely converted to propylene glycol. If contained in the mixture provided in (a), formaldehyde is essentially completely converted to methanol, acetaldehyde is essentially completely converted to ethanol, and 1,1-dimethoxyethane is essentially completely converted to methanol and ethanol. If contained in the mixture provided in (a) in traces, hydrogen peroxide present is reduced to water.

As mentioned above, after a certain operating time of the supported noble metal catalyst in (b), a decrease of its original catalytic activity will be observed. The catalytic activity of the supported noble metal catalyst may be monitored by determining the conversion rate of at least one starting material, preferably the hydroperoxypropanol, in the course of the treating in (b) at a given hydrogenation reaction temperature. Generally, it may be conceivable that such a gradual decrease of catalytic activity may be compensated to a certain extent by varying either the reaction temperature and/or the reaction pressure. However, increasing temperature and/or pressure renders the overall process less advantageous, and usually, will not be sufficient to compensate comparatively high catalytic activity decreases.

Therefore, the regeneration process of the present invention is preferably carried out if the catalyst is deactivated to an undesired extent, in particular if it exhibits a conversion rate, based on the hydroperoxypropanol, of at most 90%, preferably at most 85%, more preferably at most 80%, relative to the conversion rate of the respective fresh catalyst.

Step (c)

For regenerating the deactivated supported noble metal catalyst, the mixture obtained in (b) containing water, the organic solvent and propylene glycol is separated from the catalyst. The removal of the mixture obtained in (b) from the reactor may be achieved by any suitable method. If the treating in (b) is carried out in continuous mode, the separating according to (c) is achieved by stopping passing the mixture provided in (a) over the catalyst and removing the residual reaction mixture from the reactor in which the treating in (b) is performed; the deactivated catalyst then remains in the reactor. If the treating in (b) is carried out in batch mode, the separating in (c) is preferably performed by filtration, centrifugation, decantation, evaporation, or combinations of two or more of these methods.

After the separation of the mixture obtained in (b) from the deactivated supported noble metal catalyst and prior to (b), it is generally conceivable to subject the deactivated catalyst to a washing stage using a suitable washing agent such as water in order to remove residual reaction mixture obtained in (b) from the deactivated catalyst.

Preferably, after having separated the reaction mixture obtained in (b) from the deactivated catalyst, the deactivated catalyst is directly passed to step (d) of the process of the present invention, without any washing stage, preferably without any intermediate treatment. The term "intermediate treatment" as used in this context of the present invention relates to any treatment of the deactivated catalyst between the separation in step (c) and the contacting in (d).

Step (d)

According to step (d), the separated deactivated supported noble metal catalyst is contacted in (d) with a liquid aqueous system at a temperature in the range of from 90 to 160° C., wherein the pH of the aqueous system is outside the range of from 6 to 8. This temperature is to be understood as the temperature of the liquid aqueous system.

Preferably, in step (c), the deactivated supported noble metal catalyst is removed from the reactor and the regeneration is performed outside the reactor, preferably outside the reactor in batch mode. After the removal from the reactor, the deactivated supported noble metal catalyst is transferred into a suitable vessel and admixed with the liquid aqueous system. Preferably, the vessel is designed to be sealable in such a way that the treating according to (d) can be carried out in a closed system. More preferably, the vessel is part of an autoclave or is an autoclave. Therefore, the contacting in (d) is preferably performed in a closed system, preferably in an autoclave, preferably under autogenous pressure.

The temperature at which the contacting in (d) is carried out is suitably chosen so as to allow the aqueous system to remain in its liquid state during the contacting. Preferably, the temperature of the liquid aqueous system at which the treating is carried out is in the range of from 100 to 150° C., more preferably from 105 to 140° C., more preferably from 110 to 130° C., more preferably from 115 to 125° C.

The heating of the liquid aqueous system can be achieved by any conceivable means. Preferably, the liquid aqueous system is admixed with the deactivated supported noble metal catalyst, preferably in the vessel, and the resulting mixture is heated to the above-mentioned preferred temperature. Thus heating can be achieved, for example, by internal and/or external heating means, with external heating means being preferred. Such external heating means can be realized, for example, by a vessel comprising a jacket through which a hot fluid medium is passed transferring heat from the outside to the inside of the vessel. By suitably choosing the temperature and/or the feed rate of such a hot fluid medium, the temperature of the liquid aqueous system comprising the supported noble metal catalyst and contained in the vessel can be adjusted to the above-mentioned preferred value.

The autogenous pressure under which the treating in (d) is carried out is typically in the range of from 1 to 7 bar, such as from 1.3 to 5 bar or from 1.5 to 4 bar.

Preferably, the contacting in (d) is performed for a time period in the range of from 0.1 to 10 h, more preferably from 0.2 to 7 h, more preferably from 0.5 to 5 h. Preferred ranges are from 1 to 5 h or from 2 to 5 h or from 3 to 5 h.

Preferably, the weight ratio of the liquid aqueous system relative to the deactivated supported noble metal catalyst is in the range of from 1 to 50, more preferably from 2 to 30, more preferably from 3 to 25.

During contacting in (d), it is possible to stir the liquid aqueous system containing the supported noble metal catalyst.

Alternatively, the contacting in (d) can be performed in the reactor of (b) containing the deactivated supported noble metal catalyst separated from the mixture obtained in (b) according to (c). According to this alternative, the liquid aqueous system may be introduced via a suitable inlet so that the supported noble metal catalyst is completely immersed therein. Preferably, the regeneration in the reactor is performed in batch-mode. This implies that after introducing the aqueous system and immersing the supported noble metal catalyst therein, the respective inlet and outlet openings are sealed for the time period of the regeneration.

Preferably, the contacting in (d) in the reactor is performed under autogenous pressure, preferably at a pressure in the range of from 1 to 7 bar, more preferably from 1.3 to 5 bar, more preferably from 1.5 to 4 bar. Preferably, the contacting in (d) in the reactor is performed at a temperature in the range of from 100 to 150° C., more preferably from 105 to 140° C., more preferably from 110 to 130° C., more preferably from 115 to 125° C.

Preferably, the contacting in (d) in the reactor is performed for a time period in the range of from 5 to 10 h, preferably from 0.5 to 7 h. It is particularly preferred that the regeneration in the reactor is performed for a time period in the range of from 0.5 to 5 h.

Further, it is conceivable to carry out the regeneration in the reactor of (b) containing the deactivated supported noble metal catalyst separated from the mixture obtained in (b) according to (c) wherein the liquid aqueous system is passed over the catalyst in continuous mode. According to this alternative representing an open system, the temperature of the liquid aqueous system is suitably chosen and is preferably in the range of from 90 to less than 100° C. such as from 90 to 95° C.

Preferably, the liquid aqueous system used in (d) is not a mixture obtained in any of the stages of the epoxidation reaction according to which the mixture is preferably provided in (a), nor of any of the other stages of the process described herein. Therefore, the present invention also relates to the process as defined above, wherein the liquid aqueous system used in (d) is prepared specifically for the purpose of the treatment according to (d).

Acidic Conditions

According to a preferred embodiment of the present invention, the contacting in (d) is performed using a liquid aqueous system having a pH which is below 6, and thus, the contacting in (d) is performed under acidic conditions. Preferably, the pH of the liquid aqueous system in (d) is in the range of from 0 to 5.5, more preferably from 0 to 5, more preferably from 0 to 4.5, more preferably from 0 to 4, more preferably from 0 to 3.5, more preferably from 0 to 3, more preferably from 0 to 2.5. The pH is to be understood as being measured with a pH sensitive glass electrode.

Generally, no specific restrictions exist which acidic compounds are comprised in the liquid aqueous system, provided that the preferred pH values of the acidic conditions are achieved. Generally, it is also conceivable that in addition to the acidic compound, the liquid aqueous system contains a basic compound, provided that the preferred pH values of the acidic conditions are achieved. Preferably, the liquid aqueous system in (d) contains an acidic compound selected from the group consisting of inorganic acids, organic acids and combinations of two or more thereof, preferably from the group consisting of monovalent inorganic acids, divalent inorganic acids, trivalent inorganic acids, $C_1$-$C_{10}$ monocarboxylic acids, $C_2$-$C_{10}$ dicarboxylic acids, and combinations of two or more thereof.

Monovalent inorganic acids are preferably selected from the group consisting of hydrochloric acid, hypochloric acid, perchloric acid, hydrobromic acid, hypobromic acid, nitric acid, nitrous acid, and a combination of two or more thereof. Divalent mineral acids are preferably selected from the group consisting of carbonic acid, sulfurous acid, sulfuric acid, disulfuric acid, and a combination of two or more thereof. A preferred trivalent mineral acid is boric acid.

Preferably, the $C_{1-10}$ monocarboxylic acids are selected from the group consisting of linear or branched, saturated or unsaturated, substituted or unsubstituted $C_{1-10}$ aliphatic monocarboxylic acids, saturated or unsaturated, substituted or unsubstituted $C_{4-10}$ cycloaliphatic monocarboxylic acids, substituted or unsubstituted $C_5$-$C_{10}$ aryl monocarboxylic acids, substituted or unsubstituted $C_5$-$C_{10}$ aralkyl monocarboxylic acids, substituted or unsubstituted $C_5$-$C_{10}$ alkaryl monocarboxylic acids, and a combination of two or more thereof. More preferably, the $C_1$-$C_{10}$ monocarboxylic acids are selected from the group consisting of formic acid, acetic acid, fluoroacetic acid, chloroacetic acid, propionic acid, butyric acid, benzoic acid, and a combination of two or more thereof.

Preferably, the $C_2$-$C_{10}$ dicarboxylic acids are selected from the group consisting of linear or branched, saturated or unsaturated, substituted or unsubstituted aliphatic $C_{2-10}$ dicarboxylic acids, saturated or unsaturated, substituted or unsubstituted cycloaliphatic $C_{5-10}$ dicarboxylic acids, substituted or unsubstituted aryl $C_5$-$C_{10}$ dicarboxylic acids, substituted or unsubstituted aralkyl $C_5$-$C_{10}$ dicarboxylic acids, substituted or unsubstituted alkaryl $C_5$-$C_{10}$ dicarboxylic acids, and a combination of two or more thereof. More preferably, the $C_2$-$C_{10}$ dicarboxylic acids used in the aqueous system in (d) are selected from the group consisting of oxalic acid, malonic acid, succinic acid, glutaric acid, fumaric acid, maleic acid, phthalic acid, isophthalic acid, therephthalic acid, and a combination of two or more thereof.

According to the present invention, it is preferred that under acidic conditions in (d), the liquid aqueous system comprises, as acidic compound, more preferably as the only acidic compound, a $C_{2-10}$ dicarboxylic acid, more preferably a $C_{2-10}$ dicarboxylic acid selected from the group consisting of oxalic acid, malonic acid, succinic acid, glutaric acid, fumaric acid, maleic acid, phthalic acid, isophthalic acid, therephthalic acid, and a combination of two or more thereof. More preferably, under acidic conditions in (d), the liquid aqueous system comprises, as acidic compound, more preferably as the only acidic compound, oxalic acid.

The amounts of the one or more acidic compounds are suitably chosen by the skilled person so that the preferred pH values of the liquid aqueous system is in the above-mentioned preferred ranges of the acidic conditions.

Preferably, at least 95 weight-%, more preferably at least 96 weight-%, more preferably at least 97 weight-%, more preferably at least 98 weight-%, more preferably at least 99 weight, more preferably at least 99.5 weight-%, more preferable at least 99.9 weight-% of the liquid aqueous system consist of water and the acidic compound and optionally the basic compound, preferably of water and the acidic compound.

Preferably, the liquid aqueous system used for regeneration of the supported noble metal catalyst in (d) does not comprise an acidic compound comprising phosphorus and does not comprise a basic compound comprising phosphorus.

Basic Conditions

According to a preferred embodiment of the present invention, the contacting in (d) is performed using a liquid aqueous system having a pH which is above 8, and thus, the contacting in (d) is performed under basic conditions. Preferably, the pH of the liquid aqueous system in (d) is in the range of from 8.5 to 14, more preferably from 8.5 to 13.5, more preferably from 8.6 to 13, more preferably from 8.7 to 12.5, more preferably from 8.8 to 12, more preferably from 8.9 to 11.5, more preferably from 9 to 11. The pH is to be understood as being measured with a pH sensitive glass electrode.

Generally, no specific restrictions exist which basic compounds are comprised in the liquid aqueous system, provided that the preferred pH values of the basic conditions are achieved. Generally, it is also conceivable that in addition to the basic compound, the liquid aqueous system contains an acidic compound, provided that the preferred pH values of the basic conditions are achieved. Preferably, the liquid aqueous system in (d) contains a basic compound selected from the group consisting of inorganic bases, organic bases, and combinations of two or more thereof, preferably from the group consisting of monovalent inorganic bases, divalent inorganic bases, trivalent inorganic bases, $C_1$-$C_{10}$ organic bases, and combinations of two or more thereof.

Preferably, the inorganic bases are selected from the group consisting of ammonia, sodium hydroxide, potassium hydroxide, sodium nitrate, calcium hydroxide, disodium carbonate, sodium bicarbonate, and a combination of two or more thereof.

Preferably, the $C_1$-$C_{10}$ organic bases are selected from the group consisting of linear or branched, saturated or unsaturated, substituted or unsubstituted $C_2$-$C_{10}$ aliphatic bases, saturated or unsaturated, substituted or unsubstituted $C_{5-10}$ cycloaliphatic bases, which may comprise at least one heteroatom as a ring member, substituted or unsubstituted $C_5$-$C_{10}$ aryl bases, which may comprise at least one heteroatom as ring member, substituted or unsubstituted $C_5$-$C_{10}$ aralkyl bases, which may comprise at least one heteroatom as ring member, substituted or unsubstituted $C_5$-$C_{10}$ alkaryl bases, which may comprise at least one heteroatom as ring member, and combinations of two or more thereof, wherein the heteroatom is preferably selected from the group consisting of N, O and S. More preferably, the $C_2$-$C_{10}$ organic bases are selected from the group consisting of sodium ethanolate, sodium acetate, methyl amine, imidazole, benzimidazole, histidine, and a combination of two or more thereof.

According to the present invention, it is preferred that under basic conditions in (d), the liquid aqueous system comprises, as basic compound, more preferably as the only basic compound, a basic compound selected from the group consisting of monovalent inorganic bases, divalent inorganic bases, trivalent inorganic bases, and a combination of two or more thereof, more preferably selected from the group consisting of ammonia, sodium hydroxide, potassium hydroxide, sodium nitrate, calcium hydroxide, disodium carbonate, sodium bicarbonate, and a combination of two or more thereof. More preferably, under basic conditions in (d), the liquid aqueous system comprises, as basic compound, more preferably ammonia.

Preferably, at least 95 weight-%, more preferably at least 96 weight-%, more preferably at least 97 weight-%, more preferably at least 98 weight-%, more preferably at least 99 weight, more preferably at least 99.5 weight-%, more preferable at least 99.9 weight-% of the liquid aqueous system consist of water and the basic compound and optionally the acidic compound, preferably of water and the basic compound.

Preferably, the liquid aqueous system used for regeneration of the supported noble metal catalyst in (d) does not comprise an acidic compound comprising phosphorus and does not comprise a basic compound comprising phosphorus.

The amounts of the one or more basic compounds are suitably chosen by the skilled person so that the preferred pH values of the liquid aqueous system is in the above-mentioned preferred ranges of the basic conditions.

Step (e)

According to step (e) of the present invention, the liquid aqueous system is separated from the supported noble metal catalyst. If the contacting in (d) is carried out in continuous mode, for example in the reactor used in (b), the separating according to (e) is achieved by stopping passing the liquid aqueous system over the catalyst and removing the residual liquid aqueous system from the reactor in which the contacting in (d) is performed; the catalyst then remains in the reactor. If the contacting in (d) is carried out in batch mode, for example in a vessel, preferably in an autoclave, the separating in (e) is preferably performed by filtration, centrifugation, decantation, evaporation, or combinations of two or more of these methods.

After the separation of the liquid aqueous system, from the supported noble metal catalyst, the catalyst is preferably washed with a suitable washing agent. Preferably, the washing agent comprises water. More preferably, the washing agent essentially consists of water. More preferably, the washing agent is deionized water. Preferably, the catalyst is washed to a neutral pH. Preferably, the washing is performed until the washing water has a pH in the range of from 6.5 to 8.5. This pH is to be understood as being determined using a pH sensitive glass electrode.

If the contacting in (d) is carried out in the reactor of step (b), the washing of the supported noble metal catalyst contained in the reactor is preferably performed in continuous mode. The washing agent, preferably the deionized water, is preferably passed over the catalyst in the reactor until the water leaving the reactor has a pH in the range of from 6.5 to 8.5.

If the contacting in (d) is carried out outside the reactor of (b), preferably in a vessel, more preferably in an autoclave, the washing in (e) can be carried out in the vessel, preferably in the autoclave, and/or outside the vessel. Preferably, the catalyst having been contacted with the liquid aqueous system is suitably removed from the vessel, preferably from the autoclave, and transferred into a suitable filter, in which filter the catalyst is continuously washed, preferably until the deionized water has a pH in the range of from 6.5 to 8.5.

Preferably, after the washing or, if no washing is performed, after the contacting in (d) and after having separated the catalyst from the liquid aqueous system, the catalyst is suitably dried. The drying of the catalyst is preferably performed in a suitable atmosphere having a temperature preferably in the range of from 10 to 150° C., more preferably from 15 to 130° C., more preferably from 20 to 120° C. Conceivable preferred ranges are from 10 to 40° C. or from 15 to 35° C. or from 20 to 30° C., or from 50 to 150° C. or from 70 to 130° C. or from 90 to 120° C. Preferably, the atmosphere under which the drying is carried out comprises, preferably is air or nitrogen. More preferably, the atmosphere is nitrogen, more preferably technical nitrogen. The drying can be carried out under static conditions in a suitable apparatus such as an oven or the like. Further, the drying can be carried out continuously, for example by passing the atmosphere over the catalyst at a suitable flow rate. Preferably, the flow rate is in the range of from 0.1 to 100 Nl/h, more preferably from 1 to 80 Nl/h, more preferably from 2 to 50 Nl/h.

Preferably, the drying is performed for a period of time in the range of from 1 to 250 hours, 5 to 200 h, preferably from 10 to 180 h, more preferably from 15 to 150 h, even more preferably from 20 to 50 h.

During the drying, it is possible to keep the drying temperature constant, or to change the drying temperature continuously or discontinuously.

Step (f)

After step (e), preferably after washing or after drying, more preferably after washing and drying, the supported noble metal catalyst is subjected to calcination.

The calcination of the supported noble catalyst can be effected under any suitable gas atmosphere, wherein air or lean air preferred, with air being especially preferred. The calcination is preferably carried out in a muffle furnace, rotary furnace and/or a belt calcination furnace. Preferably, the temperature of the atmosphere the catalyst is brought into contact with is above 200° C., more preferably above 210° C., more preferably above 220° C. Preferably, the calcination temperature is at most 700° C., more preferably at most 600° C., more preferably at most 500° C., more preferably at most 475° C. Therefore, the present invention relates to the process as described above, wherein the calcination temperature is in the range of from 200 to 700° C., preferably from 220 to 475° C. Preferred ranges are from 200 to 300° C., preferably from 210 to 290° C., more preferably from 220 to 280° C., more preferably from 230 to 270° C., or from 400 to 500° C., preferably from 410 to 490° C., more preferably from 420 to 480° C., more preferably from 430 to 470° C.

The calcination is generally carried out for 0.25 h or more, for example for a time period in the range of from 0.25 to 12 hours, preferably from 0.5 to 6 hours, more preferably from 0.5 to 4 h, more preferably from 1 to 3 h.

During calcination, it is possible to keep the calcination temperature constant, or to change the calcination temperature continuously or discontinuously.

Step (g)

Generally, the catalyst obtained from the calcination in (f) can be used again, preferably as a catalyst in the treating according to (b). Optionally, before recycling the catalyst as regenerated catalyst to (b), the calcined catalyst obtained from (f) can be suitably activated. Therefore, the present invention also relates to the process as described above, further comprising (g) activating the catalyst obtained from (f).

Regarding this activation, any suitable activation method is generally conceivable. Preferably, the catalyst obtained from (f) is activated by subjecting the catalyst to reducing conditions, preferably to reducing conditions in the presence of hydrogen. Therefore, the activation according to (g) preferably comprises treating the catalyst obtained from (f) with hydrogen. It is possible that the activation according to (g) preferably consists of treating the catalyst obtained from (f) with hydrogen.

When treating the catalyst with hydrogen, it is possible that the treating is carried out in the presence of an inert gas.

Preferably, the inert gas is selected from the group consisting of nitrogen, helium, neon, argon, carbon dioxide, and combinations of two or more thereof. Preferably, one single inert gas is used. More preferably, the inert gas is nitrogen.

The treatment of the supported noble metal catalyst with the hydrogen can be carried out at any suitable temperature. Preferably, the treating is carried out at temperatures elevated with respect to room temperature, preferably at a temperature in the range of from 100 to 150° C., more preferably from 110 to 130° C.

Generally, it is possible that the treatment with hydrogen is carried out in batch mode in a suitable vessel such as the autoclave described hereinabove. In this case, the treatment with hydrogen is preferably performed for a period of time in the range of from 1 to 24 h, preferably from 2 to 24 h, more preferably for 6 to 18 h. Preferably, the treatment with hydrogen is carried out in continuous mode, more preferably in the reactor in which the catalyst is to be used after the activation. Therefore, it is preferred to treat the catalyst obtained from (f) with hydrogen in the reactor in (b). In this case, the hydrogen is brought into contact with the catalyst to be activated generally at from 10 to 1500 $l_{hydrogen}$ $kg^{-1}_{catalyst}$ $h^{-1}$, preferably from 50 to 1200 $l_{hydrogen}$ $kg^{-1}_{catalyst}h^{-1}$.

As mentioned above, it is especially preferred to employ the regenerated catalyst in step (b) of the process of the present invention. When the deactivated catalyst is taken out from operation to be subjected to regeneration according to steps (c) to (f), optionally steps (c) to (g) of the present invention, it is preferred that at least one further reactor according to (b) is present which guarantees that the preferred epoxidation process and the downstream work-up stages do not have to be interrupted and the preferred overall continuous process can be continued. Thus, it is preferred that while the supported noble metal catalyst contained in a first reactor according to (b) is regenerated and thus taken out of operation, the treating according to (b) is continued in at least one further reactor according to (b).

According to the present invention, it is conceivable that only a portion of the regenerated catalyst is recycled to (b) and, for the purpose of the treating in (b), is admixed with fresh catalyst.

After step (b) of the process of the present invention, the reaction mixture obtained is preferably subjected to further work-up stages. Preferably, the further work-up stages are directed to the work-up and the recycling of the organic solvent, preferably methanol or acetonitrile, more preferably methanol. More preferably, these downstream work-up stages may include (b1) adding a base to the mixture obtained in (b) to obtain a mixture (Mb1), wherein an aqueous alkaline solution comprising hydroxide ions is preferably added as base;

(b2) separating methanol from mixture (Mb1) by distillation;

(b3) at least partially recycling the methanol obtained from (b1) as solvent into the epoxidation according to (a).

In (b2), methanol is separated from mixture (Mb1) preferably by (b21) separating at least one compound comprised in (Mb1) having a boiling temperature lower than methanol and lower than water from mixture (Mb1), preferably selected from the group consisting of formaldehyde, acetaldehyde, propionaldehyde, methyl formate, formaldehyde dimethyl acetal, acetaldehyde, and dimethyl acetal by distillation to obtain a mixture (Mb11) and a mixture (Mb12), wherein mixture (Mb11) comprises from 40 to 85 weight-% methanol and from 10 to 55 weight-% water and at most 0.1 weight-% of the at least one compound having a boiling point lower than methanol and water, and wherein mixture (Mb12) comprises at least 5 weight-% of the at least one compound having a boiling point lower than methanol;

(b22) separating methanol from mixture (Mb11) in at least one distillation stage to obtain a mixture comprising at least 85 weight-% of methanol, up to 10 weight-% of water and 200 ppm or less of carbonyl compounds, and a mixture comprising at least 90 weight-% of water.

The Regenerated Supported Noble Metal Catalyst

Yet further, the present invention relates to a supported noble metal catalyst obtainable or obtained by the process of the present invention as described above.

Preferably, the catalyst regenerated according to the process of the present invention exhibits a differential conversion rate of at most 5, preferably of at most 4, wherein the differential conversion rate is defined as the difference in percentage points between (i) the conversion rate based on the hydroperoxypropanol in said process for the hydrogenation of hydroperoxypropanol in which the regenerated catalyst is used as catalyst, and (ii) the conversion rate based on the hydroperoxypropanol agent in said process for hydrogenation of hydroperoxypropanol in which the respective fresh catalyst is used as catalyst, said process for hydrogenation of hydroperoxypropanol being carried out under otherwise identical hydrogenation conditions compared with the process for hydrogenation of hydroperoxypropanol according to (i).

Still further, the present invention relates to the use of the regenerated catalyst according to the present invention for the hydrogenation of a hydroperoxypropanol.

In particular, the present invention is characterized by the following embodiments, including the combinations of embodiments as indicated by the respective dependencies:

1. A process for the regeneration of a supported noble metal catalyst having been used in a process comprising
   (a) providing a mixture containing water, an organic solvent and a hydroperoxypropanol;
   (b) treating the mixture provided in (a) in a reactor under reducing conditions with hydrogen in the presence of the supported noble metal catalyst to obtain a mixture containing water, the organic solvent and propylene glycol;
   said process for the regeneration comprising
   (c) separating the mixture obtained from (b) from the catalyst;
   (d) contacting the separated catalyst with a liquid aqueous system at a temperature in the range of from 90 to 160° C., wherein the pH of the aqueous system is outside the range of from 6 to 8;
   (e) separating the liquid aqueous system from the catalyst;
   (f) subjecting the catalyst to calcination.

2. The process of embodiment 1, wherein the hydroperoxypropanol contained in the mixture provided in (a) is selected from the group consisting of 2-hydroperoxypropanol-1,1-hydroperoxypropanol-2, and a combination thereof.

3. The process of embodiment 1 or 2, wherein the mixture provided in (a) contains the hydroperoxypropanol in an amount in the range of from 0.1 to 1 weight-% based on the weight of the mixture.

4. The process of any of embodiments 1 to 3, wherein the mixture provided in (a) additionally contains a further oxygenate in an amount in the range of from 0.1 to 1 weight-%, preferably from 0.1 to 0.5 weight-% based on the weight of the mixture, wherein the further oxygenate is preferably selected from the group consisting of formaldehyde, acetaldehyde, propionaldehyde, hydroxyacetone, methylformate, dimethoxymethane, and combinations of two or more thereof.

5. The process of any of embodiments 1 to 4, wherein the mixture provided in (a) contains the water in an amount in the range of from 10 to 40 weight-% and the organic solvent in an amount in the range of from 55 to 85 weight-%, based on the weight of the mixture, wherein preferably at least 95 weight-%, more preferably from 95 to 98 weight-% of the mixture consist of water and the organic solvent.

6. The process of any of embodiments 1 to 5, wherein the organic solvent contained in the mixture provided in (a) is selected from the group consisting methanol and acetonitrite, the organic solvent preferably being methanol.

7. The process of any of embodiments 1 to 6, wherein the noble metal of the supported noble metal catalyst is selected from the group consisting of palladium, platinum, rhodium, iridium, osmium and combinations of two or more thereof, preferably from the group consisting of palladium supported on alumina, preferably alpha-alumina, and palladium supported on activated carbon, wherein the catalyst contains the noble metal preferably in an amount of from 0.1 to 1.0 weight-%, more preferably from 0.2 to 0.5 weight-%, based on the weight of the catalyst.

8. The process of any of embodiments 1 to 7, wherein the treating in (b) is carried out at a temperature in the range of from 25 to 120° C., preferably from 50 to 85° C., and a pressure in the range of from 1 to 100 $bar_{abs}$, preferably from 1 to 10 $bar_{abs}$, preferably under an inert gas atmosphere, the inert gas preferably being nitrogen.

9. The process of any of embodiments 1 to 8, wherein the separating in (c) is performed by filtration, centrifugation, decantation, evaporation, or by a combination of two or more thereof.

10. The process of any of embodiments 1 to 9, wherein the contacting in (d) is performed in a closed system, preferably in an autoclave, under autogenous pressure, preferably at a temperature in the range of from 100 to 150° C., more preferably from 110 to 130° C.

11. The process of any of claims 1 to 9, wherein the contacting in (d) is performed in the reactor of (b) containing the catalyst separated according to (c) from the mixture obtained in (b).

12. The process of any of embodiments 1 to 11, wherein the contacting in (d) is performed for a period of time in the range of from 0.1 to 10 h, preferably from 0.2 to 7 h, more preferably from 0.5 to 5 h.

13. The process of any of embodiments 1 to 12, wherein the pH of the liquid aqueous system in (d) is in the range of from 0 to 5.5, preferably from 0 to 2.5.

14. The process of embodiment 13, wherein the liquid aqueous system in (d) contains an acidic compound selected from the group consisting of inorganic acids, organic acids and combinations of two or more thereof, preferably from the group consisting of monovalent inorganic acids, divalent inorganic acids, trivalent inorganic acids, $C_1$-$C_{10}$ monocarboxylic acids, $C_2$-$C_{10}$ dicarboxylic acids, and combinations of two or more thereof.

15. The process of any of embodiments 1 to 12, wherein the pH of the liquid aqueous system in (d) is in the range of from 8.5 to 14, preferably from 9 to 11.

16. The process of embodiment 15, wherein the liquid aqueous system in (d) contains a basic compound selected from the group consisting of inorganic bases, organic bases, and combinations of two or more thereof, preferably from the group consisting of monovalent inorganic bases, divalent inorganic bases, trivalent inorganic bases, $C_1$-$C_{10}$ organic bases, and combinations of two or more thereof.

17. The process of any of embodiments 1 to 16, wherein the liquid aqueous system used in (d) does not comprise an acidic compound comprising phosphorus and does not comprise a basic compound comprising phosphorus.

18. The process of any of embodiments 1 to 17, wherein the separating in (e) is performed by filtration, centrifugation, decantation, evaporation, or by a combination of two or more thereof.

19. The process of embodiment 18, wherein the separating in (e) further comprises washing the separated catalyst and preferably drying the washed catalyst, the drying preferably being carried out at a temperature in the range of from 10 to 150° C., more preferably from 15 to 130° C., more preferably from 20 to 120° C.

20. The process of any of embodiments 1 to 19, wherein in (f), the catalyst is subjected to calcination at a temperature in the range of from 200 to 700° C., preferably from 220 to 475° C., preferably in air.

21. The process of any of embodiments 1 to 20, wherein in (f), the catalyst is subjected to calcination for a period of time in the range of from 0.5 to 4 h, preferably from 1 to 3 h.

22. The process of any of embodiments 1 to 21, further comprising
(g) activating the catalyst obtained from (f).

23. The process of embodiment 22, wherein the activating in (g) comprises treating the catalyst with hydrogen, optionally in the presence of an inert gas, preferably nitrogen, at a temperature in the range of from 100 to 150° C., preferably from 110 to 130° C.

24. The process of any of embodiments 1 to 23, wherein the mixture provided in (a) is obtained by a process for the epoxidation of propene, said process comprising reacting propene with hydrogen peroxide in the presence of the organic solvent and a titanium zeolite catalyst, and separating propylene oxide and optionally propene from the resulting epoxidation reaction mixture to obtain the mixture provided in (a).

25. The process of embodiment 24, wherein the titanium zeolite catalyst comprises titanium silicalite-1 (TS-1) and/or Ti-MWW, preferably TS-1, the organic solvent is methanol or acetonitrile, preferably methanol.

26. The process of embodiments 24 or 25, wherein the propene is employed as a mixture comprising propene and propane and wherein propylene oxide, propane and optionally propene are separated from the resulting epoxidation reaction mixture to obtain the mixture provided in (a).

27. The process of any of embodiments 1 to 26, comprising employing the catalyst obtained from (f) or (g) as catalyst in a process comprising (b).

28. The process of embodiment 27, wherein in the process comprising (b), the catalyst obtained from (f) or (g) exhibits a differential conversion rate of at most 5, preferably of at most 4, wherein the differential conversion rate is defined as the difference in percentage points between
(i) the conversion rate based on the hydroperoxypropanol in said process comprising (b) in which the catalyst obtained from (f) or (g) is used as catalyst, and (ii) the conversion rate based on the hydroperoxypropanol in said process comprising (b) in which the respective fresh catalyst is used as catalyst, said process comprising (b) being carried out under otherwise identical hydrogenation conditions compared with the process comprising (b) according to (i).

29. A regenerated supported noble metal catalyst, obtainable or obtained by a process according to any of embodiments 1 to 26.

30. The regenerated supported noble metal catalyst of embodiment 29, wherein in a process for the hydrogenation of hydroperoxypropanol, the regenerated catalyst exhibits a differential conversion rate of at most 5, preferably of at most 4, wherein the differential conversion rate is defined as the difference in percentage points between
   (i) the conversion rate based on the hydroperoxypropanol in said process for the hydrogenation of hydroperoxypropanol in which the regenerated catalyst is used as catalyst, and
   (ii) the conversion rate based on the hydroperoxypropanol agent in said process for hydrogenation of hydroperoxypropanol in which the respective fresh catalyst is used as catalyst, said process for hydrogenation of hydroperoxypropanol being carried out under otherwise identical hydrogenation conditions compared with the process for hydrogenation of hydroperoxypropanol according to (i).

31. Use of a regenerated catalyst according to embodiment 29 or 30 for the hydrogenation of a hydroperoxypropanol.

The present invention is illustrated by the following examples.

EXAMPLES

A Regeneration of a Catalyst Used in the Hydrogenation of a Hydroperoxypropanol in a Mixture Further Containing Acetonitrile and Water The deactivated catalyst used in Comparative Example A1 and further in Examples A1 and A2 originated from a process for the epoxidation of propene to yield propylene oxide. The epoxidation was carried out in the presence of a catalyst comprising a TiMWW zeolite. As solvent, acetonitrile was employed. An aqueous hydrogen peroxide solution was employed as epoxidation agent. Propene as starting material was used as a mixture of propene and propane. The reaction mixture obtained was subjected to a separation stage where unreacted propene and propane were separated off by distillation as low boilers.

The resulting mixture comprising acetonitrile, water, and propylene oxide was subjected to a downstream separation stage where propylene oxide was distilled off as low boiler. The thus obtained liquid mixture contained acetonitrile (81 weight-%), water (18 weight-%) and hydroperoxypropanol (0.5 weight-%) and traces of further oxygenates including acetaldehyde, propylenoxide, propionaldehyde, acetamide, acetone, 1-(2-hydroxypropoxy)propan-2-ol, tripropyleneglycol, propylene glycol, hydroxyacetone, formaldehyde, 2,4-dimethyl-4,5-dihydrooxazole, 2,5-dimethyl-4,5-dihydrooxazole, acetoxyacetone, cis- and trans-2-ethyl-4-methyl-1,3-dioxolane, 2-pentanone, 2-hexanone, pentanenitrile, 2,6-dimethyl-4-heptanone, 4,6-dimethyl-2-heptanol, butanone, 1-nitropropane, 2-nitropropane, 4-methyl-1,3-dioxolane, 2-propanol, 2-pentanol, 3-methylbutanenitrile. This liquid mixture was used as starting mixture subjected to hydrogenation.

The hydrogenation catalyst consisted of 0.3 weight-% palladium supported on alpha-alumina (0.3% $Pd/Al_2O_3$). The catalyst was used in the form of strands having a diameter of 4 mm. Before starting a hydrogenation reaction, the fresh catalyst was activated in the reactor at 115° C. and 15 bar for 18 hours in a gas stream comprising a mixture of hydrogen (25 Nl/min) and nitrogen (10 Nl/min) (Nl=norm liter).

The hydrogenation catalyst was in use for 3787 hours. After said 3787 hours, the deactivated catalyst was removed from the reactor. Portions of the deactivated catalyst were subjected to different regeneration processes, followed by determination of the respective catalytic activity.

Comparative Example A1

Regeneration of the Deactivated Catalyst by Activation with Hydrogen Only

For comparative Example A1, 25 g of the deactivated $Pd/Al_2O_3$ were transferred into a technical scale reactor. The reactor comprised four tubes of 1.5 m length having an inner diameter of 5 mm equipped with heating means. The activation of the deactivated catalyst was carried out in the reactor at 115° C. and 15 bar for 18 hours in a gas stream comprising a mixture of hydrogen (25 Nl/min) and nitrogen (10 Nl/min) (Nl=norm liter) (Sample 1).

Example A1

Regeneration of the Deactivated Catalyst by Contacting with a Liquid Basic Aqueous System 30 g of the deactivated $Pd/Al_2O_3$ catalyst were submitted to regeneration in an alkaline aqueous medium according to the invention. The catalyst was immersed in ammonia solution (10 weight-% in water, having a pH of 10.5 at 80° C.) and heated in an autoclave under autogenous pressure for 4 hours at 120° C. Following the alkaline treatment, the catalyst was washed with water to a neutral pH and dried for 16 hours at 120° C. in air. After completed drying, the catalyst was calcinated for 2 hours at 250° C. in air.

25 g of the thus treated catalyst were transferred in the technical scale reactor and activated as described in Comparative Example A1 (Sample 2).

Example A2

Regeneration of the Deactivated Catalyst by Contacting with a Liquid Acidic Aqueous System 30 g of the deactivated $Pd/Al_2O_3$ catalyst were submitted to regeneration in an acidic aqueous medium according to the invention. The catalyst was immersed in oxalic acid solution (5 weight-% in water, having a pH of 1.0 at 82° C.) and heated in an autoclave under autogenous pressure for 4 hours at 120° C. Following the acidic treatment, the catalyst was washed with water to a neutral pH and dried for 16 hours at 120° C. in air. After completed drying, the catalyst was calcinated for 2 hours at 250° C. in air.

25 g of the regenerated catalyst were transferred in the technical scale reactor and activated as described in Comparative Example A1 (Sample 3).

Example A3

Catalytic Activity of the Regenerated Catalysts

The regenerated catalysts of Comparative Example A1 and of Examples A1 and A2 (Samples 1 to 3) were used in a hydrogenation reaction performed at technical scale in the reactor described in Comparative Example 1. For further comparison, a hydrogenation of hydroperoxypropanol was performed with 25 g of fresh Pd/Al$_2$O$_3$ catalyst which had been activated prior to hydrogenation in a reactor as described in Comparative Example A1 (Sample 4).

The liquid mixture described above, containing acetonitrile, water, hydroperoxypropanol and the oxygenate traces was continuously fed into the technical scale reactor with a WHSV (weight hourly space velocity) of 16 h$^{-1}$.

A mixture of hydrogen and nitrogen was also introduced into the reactor (5 Nl/h H$_2$ and 5 Nl/h N$_2$). The reduction of hydroperoxypropanol was performed at a temperature of 70° C. and a pressure of 15 bar. The hydroperoxypropanol content was determined iodometrically according to DIN EN ISO 3960 from which the hydroperoxypropanol conversion rate was calculated.

The individual operating times and conversion rates based on hydroperoxypropanol for the individual catalyst samples are summarized in Table 1 below.

TABLE 1

The results according to Example A

| | Catalyst condition | Operating time (hours) | Hydroperoxy-propanol conversion rate (%) at end of operating time | Hydroperoxy-propanol conversion rate (%) averaged over operating time | Differential conversion rate based on averaged conversion rate (% points) |
|---|---|---|---|---|---|
| Sample 1 | deactivated/ activated | 370 | 67 | 70 | 19 |
| Sample 2 | deactivated/ regenerated/ activated | 370 | 85 | 85 | 4 |
| Sample 3 | deactivated/ regenerated/ activated | 370 | 89 | 92 | 0 |
| Sample 4 | fresh/ activated | 361 | 89 | 89 | — |

It is evident from Table 1 that a deactivated catalyst which has been activated only (Sample 1) exhibits an unfavorable hydroperoxypropanol conversion rate of only 67% at the end of an operation time of 370 hours. The hydroperoxypropanol conversion rate averaged over these 370 hours was 70%.

On the other hand, the catalysts which are regenerated according to the process of the present invention (Sample 2 and Sample 3) show a hydroperoxypropanol conversion rate of 85% and 89%, respectively, at the end of the running time of 370 hours, which corresponds to an averaged conversion rate of 85% and 92%. The catalytic activity of the supported noble metal catalyst regenerated according to the process of the present invention is therefore in the range or equal to the catalytic activity of fresh catalyst (Sample 4), for which a hydroperoxypropanol conversion rate of 89% at the end of the running time and also an average conversion rate of 89% was determined. For the consideration of the average conversion rate of Samples 1 to 4, it was disregarded that the overall running time for Sample 4 was 361 hours instead of 370 hours.

From the average conversion rates, further the differential conversion rates of Samples 1 to 3 relative to Sample 4 representing fresh catalyst were determined (right column of Table 1). Favorably, the average conversion rates of Samples 2 and 3 regenerated according to the process of the invention deviate by only 4 and 0% points from the average conversion rate of Sample 4. In contrast, the average conversion rate of comparative Sample 1 deviated from the average conversion rate of Sample 4 by 19% points.

B Regeneration of a Catalyst Used in the Hydrogenation of Hydroperoxypropanol in a Mixture Further Containing Methanol and Water The deactivated catalyst used in Comparative Example B1 and further in Example B1 and B2 originated from a process for the epoxidation of propene to yield propylene oxide. The epoxidation was carried out in the presence of a catalyst comprising a TS-1 zeolite. As solvent, methanol was employed. An aqueous hydrogen peroxide solution was employed as epoxidation agent. Propene as starting material was used as a mixture of propene and propane. The reaction mixture obtained was subjected to a separation stage where unreacted propene and propane were separated off by distillation as low boilers.

The resulting mixture comprising methanol, water, and propylene oxide was subjected to a downstream separation stage where propylene oxide was distilled off as low boiler. The resulting liquid mixture contained methanol (75 weight-%), water (22 weight-%) and hydroperoxypropanol (0.5 weight.-%) and traces of further oxygenates including ethanol, acetaldehyde, methylformiate, isopropanol, dimethoxymethane, propyleneoxide, 2-propenol, n-propanol, propionaldehyde, methylacetate, 1,1-dimethoxyethane, acetone, 1-butanol, 1,1-dimethoxypropane, 2,4-dimethyl-1, 3-dioxolane, 4-methyl-1,3-dioxolane, 1,2-dimethoxypropane, 1-methoxy-2-propanol, 2-methoxy-1-propanol, propylene glycol, hydroxyacetone, 2-methylvaleraldehyd, 2-hexanone, 2-methylcyclohexanol, 2,6-dimethyl-4-heptanone, dipropylglycolmethylether, dipropyleneglycol, tripropyleneglycol. This liquid mixture was used as starting mixture subjected to hydrogenation.

The hydrogenation catalyst consisted of 0.3 weight-% palladium supported on alpha-alumina (0.3% Pd/Al$_2$O$_3$). The catalyst was used in the form of strands having a diameter of 4 mm. Before starting a hydrogenation reaction, the fresh catalyst was activated in the reactor at 115° C. and 15 bar for 18 hours in a gas stream comprising a mixture of hydrogen (25 Nl/min) and nitrogen (10 Nl/min) (Nl=norm liter).

The hydrogenation catalyst was in use until the conversion rate with respect to hydroperoxypropanol dropped below 80% relative to the respective conversion rate of the fresh catalyst. Portions of the deactivated catalyst were subjected to different regeneration processes, followed by determination of the respective catalytic activity.

Comparative Example B1

Regeneration of the Deactivated Catalyst by Activation with Hydrogen Only

For Comparative Example B1, 25 g of the deactivated Pd/Al$_2$O$_3$ were transferred into the technical scale reactor already described in Comparative Example A1. The activation of the deactivated catalyst was carried out in the reactor at 115° C. and 15 bar for 18 hours in a gas stream comprising a mixture of hydrogen (25 Nl/min) and nitrogen (10 Nl/min) (Nl=norm liter) (Sample 5).

Example B1

Regeneration of the Deactivated Catalyst by Contacting with a Liquid Basic Aqueous System 30 g of the deactivated Pd/Al$_2$O$_3$ catalyst were submitted to regeneration in an alkaline aqueous medium according to the invention. The catalyst was immersed in ammonia solution (10 weight-% in water, having a pH of 10.5 at 80° C.) and heated in an autoclave under autogenous pressure for 4 hours at 120° C. Following the alkaline treatment, the catalyst was washed with water to a neutral pH and dried for 16 hours at 120° C. in air. After completed drying, the catalyst was calcinated for 2 hours at 450° C. in air.

25 g of the regenerated catalyst were transferred in the technical scale reactor and activated as described in Comparative Example A1 (Sample 6).

Example B2

Regeneration of the Deactivated Catalyst by Contacting with a Liquid Acidic Aqueous System 30 g of the deactivated Pd/Al$_2$O$_3$ catalyst were submitted to regeneration in an acidic aqueous medium according to the invention. The catalyst was immersed in oxalic acid solution (5 weight-% in water, having a pH of 1.0 at 82° C.) and heated in an autoclave under autogenous pressure for 4 hours at 120° C. Following the acidic treatment, the catalyst was washed with water to a neutral pH and dried for 16 hours at 120° C. in air. After completed drying, the catalyst was calcinated for 2 hours at 450° C. in air.

25 g of the regenerated catalyst were transferred in the technical scale reactor and activated as described in Comparative Example A1 (Sample 7).

Example B3

Catalytic Activity of the Regenerated Catalysts

The regenerated catalysts of Comparative Example B1 and of Examples B1 and B2 (Samples 5 to 7) were used in a hydrogenation reaction performed at technical scale in the reactor described in Comparative Example 1. For further comparison, a hydrogenation of hydroperoxypropanol was also performed with 25 g fresh Pd/Al$_2$O$_3$ catalyst (Sample 8) which had been activated before in a reactor as described in Comparative Example A1.

The liquid mixture described above, containing methanol, water, hydroperoxypropanol and the oxygenate traces was continuously fed into the technical scale reactor with a WHSV of 16 h$^{-1}$. A mixture of hydrogen and nitrogen was also introduced into the reactor (5 Nl/h H$_2$ and 5 Nl/h N$_2$). The reduction of hydroperoxypropanol was performed at a temperature of 55° C. and a pressure of 15 bar. The hydroperoxypropanol content was determined iodometrically according to DIN EN ISO 3960 from which the hydroperoxypropanol conversion rate was calculated.

The individual operating times and conversion rates based on hydroperoxypropanol for the individual catalyst samples are summarized in Table 2 below.

TABLE 2

The results according to Example B

| | Catalyst condition | Operating time (hours) | Hydroperoxypropanol conversion rate (%) at end of operating time | Average hydroperoxypropanol conversion rate (%) over operating time |
|---|---|---|---|---|
| Sample 5 | deactivated/activated | 191 | 87 | 88 |
| Sample 6 | deactivated/regenerated/activated | 1160 | 94 | 96 |
| Sample 7 | deactivated/regenerated/activated | 404 | 93 | 93 |
| Sample 8 | fresh/activated | 914 | 95 | 95 |

The results in Table 2 clearly show that deactivated catalyst which has been only activated has a hydroperoxypropanol conversion rate of merely 87% after 191 hours of operating time (Sample 5). The average hydroperoxypropanol conversion rate over the operating time of 191 hours was determined to be 88%.

Surprisingly, the catalysts which have been regenerated according to the process of the present invention (Sample 6 and Sample 7), show a significantly increased hydroperoxypropanol conversion rate of 94% and 93%, respectively, relative to the catalyst which has been activated only (Sample 5) following 1160 and 404 hours operating time. The catalytic activity of the supported noble metal catalyst regenerated according to the process of the present invention is therefore in the range of the catalytic activity of fresh catalyst (Sample 8), for which a hydroperoxypropanol conversion rate of 95% was determined after 914 hours running time. It is further noted that like Sample 8, the average conversion rates of Samples 6 and 7 (96% and 93%) differed only slightly or not at all from the conversion rates at the end of their respective operating times (94% and 93%), indicating a stable catalytic performance.

CITED LITERATURE

WO 02/062779 A
WO 2007/074101 A
EP 0 200 260 A
Ullmann's Encycolpedia of Industrial Chemistry, 5th edition, volume 3 (1989) pages 447-457

The invention claimed is:

1. A process for regenerating a supported noble metal catalyst, the process comprising
   (a) separating the catalyst from a mixture (A) to obtain a separated catalyst (I);
   (b) contacting the separated catalyst (I) with a liquid aqueous system at a temperature in a range of from 90 to 160° C. in a closed system under autogenous pressure, wherein a pH of the aqueous system is outside a range of from 6 to 8;
   (c) separating the liquid aqueous system from the separated catalyst (I) to obtain a separated catalyst (II); and
   (d) subjecting the separated catalyst (II) to calcination, wherein the catalyst has been used in a process comprising
      (i) providing a mixture comprising water, an organic solvent, and a hydroperoxypropanol; and
      (ii) treating the mixture provided in (i) in a reactor under reducing conditions with hydrogen in the presence of the catalyst to obtain the mixture (A) comprising water, the organic solvent, and propylene glycol.

2. The process of claim 1, wherein the mixture provided in (i) comprises the hydroperoxypropanol in an amount of from 0.1 to 1 weight-% based on a weight of the mixture.

3. The process of claim 1, wherein the mixture provided in (i) further comprises an oxygenate in an amount of from 0.1 to 1 weight-% based on a weight of the mixture.

4. The process of claim 1, wherein the mixture provided in (i) comprises water in an amount of from 10 to 40 weight-% and the organic solvent in an amount of from 55 to 85 weight-%, based on a weight of the mixture.

5. The process of claim 1, wherein the organic solvent in the mixture provided in (i) is selected from the group consisting of methanol and acetonitrile.

6. The process of claim 1, wherein the noble metal of the supported noble metal catalyst is selected from the group consisting of palladium, platinum, rhodium, iridium, osmium and a combination of two or more thereof.

7. The process of claim 1, wherein the treating (ii) is carried out at a temperature in a range of from 25 to 120° C. and a pressure in a range of from 1 to 100 $bar_{abs}$.

8. The process of claim 1, wherein the contacting (b) is performed in the reactor of (ii) comprising the separated catalyst (I).

9. The process of claim 1, wherein the contacting (b) is performed for a period of time in a range of from 0.1 to 10 h.

10. The process of claim 1, wherein the pH of the liquid aqueous system in (b) is in a range of from 0 to 5.5.

11. The process of claim 1, wherein the pH of the liquid aqueous system in (b) is in a range of from 8.5 to 14.

12. The process of claim 1, wherein the separating (a) is performed by filtration, centrifugation, decantation, evaporation, or a combination of two or more thereof, and
   wherein the separating (c) is performed by filtration, centrifugation, decantation, evaporation, or a combination of two or more thereof.

13. The process of claim 12, wherein the separating (c) further comprises
   washing the separated catalyst (I).

14. The process of claim 1, wherein in (d), the separated catalyst (II) is subjected to the calcination at a temperature in a range of from 200 to 700° C.

15. The process of claim 1, further comprising
   (e) activating the catalyst obtained from (d).

16. The process of claim 1, wherein the mixture provided in (i) is obtained by a process for epoxidizing propene comprising
   reacting propene with hydrogen peroxide in the presence of the organic solvent and a titanium zeolite catalyst to obtain an epoxidation reaction mixture, and
   separating propylene oxide from the epoxidation reaction mixture to obtain the mixture provided in (i).

17. The process of claim 1, comprising employing the catalyst obtained from (d) as a catalyst in a process comprising (ii).

* * * * *